United States Patent [19]
Zunker et al.

[11] Patent Number: 6,090,038
[45] Date of Patent: Jul. 18, 2000

[54] EXPANDABLE DOME-SHAPED URINARY INCONTINENCE DEVICE AND A METHOD OF MAKING THE SAME

[75] Inventors: MaryAnn Zunker, Oshkosh; David Arthur Fell, Neenah, both of Wis.

[73] Assignee: Kimberly-Clark Worldwide, Inc., Neenah, Wis.

[21] Appl. No.: 09/217,396

[22] Filed: Dec. 21, 1998

[51] Int. Cl.$^7$ ................................................ A61F 2/00
[52] U.S. Cl. ............................................................. 600/29
[58] Field of Search .................. 600/29, 32; 604/385.1; 128/885

[56] References Cited

U.S. PATENT DOCUMENTS

| | | | |
|---|---|---|---|
| 1,280,979 | 10/1918 | Ellis . | |
| 2,092,427 | 9/1937 | Ross | 128/285 |
| 2,201,412 | 5/1940 | Stein | 128/285 |
| 2,264,586 | 12/1941 | Ross | 128/285 |
| 2,487,200 | 11/1949 | Trager | 128/285 |
| 2,501,972 | 3/1950 | Seidler | 128/263 |
| 2,711,173 | 6/1955 | Seidler | 128/263 |
| 2,938,519 | 5/1960 | Marco | 128/285 |
| 3,011,495 | 12/1961 | Brecht | 128/285 |
| 3,051,177 | 8/1962 | Wilson | 128/285 |
| 3,079,921 | 3/1963 | Brecht et al. | 128/285 |
| 3,138,159 | 6/1964 | Schmidt | 128/285 |
| 3,369,544 | 2/1968 | Crockford | 128/285 |
| 3,469,286 | 9/1969 | Crockford | 19/144.5 |
| 3,596,328 | 8/1971 | Voss | 19/144.5 |
| 3,643,661 | 2/1972 | Crockford | 128/263 |
| 3,683,915 | 8/1972 | Voss | 128/285 |
| 3,706,311 | 12/1972 | Kokx et al. | 128/285 |
| 3,749,094 | 7/1973 | Duncan | 128/285 |
| 3,762,413 | 10/1973 | Hanke | 128/285 |
| 3,971,378 | 7/1976 | Krantz | 128/285 |
| 4,018,225 | 4/1977 | Elmi | 128/285 |
| 4,212,301 | 7/1980 | Johnson | 128/285 |
| 4,266,546 | 5/1981 | Roland et al. | 128/285 |
| 4,318,407 | 3/1982 | Woon | 128/285 |
| 4,335,721 | 6/1982 | Matthews | 128/285 |
| 4,359,357 | 11/1982 | Friese | 156/201 |
| 4,486,191 | 12/1984 | Jacob | 604/330 |
| 4,668,557 | 5/1987 | Lakes | 428/131 |
| 5,041,077 | 8/1991 | Kulick | 600/29 |
| 5,045,079 | 9/1991 | West | 604/329 |
| 5,112,348 | 5/1992 | Glassman | 604/358 |
| 5,158,535 | 10/1992 | Paul et al. | 604/15 |
| 5,273,521 | 12/1993 | Peiler et al. | 604/13 |

(List continued on next page.)

FOREIGN PATENT DOCUMENTS

19602878 C1  9/1997  Germany .

*Primary Examiner*—Max Hindenburg
*Assistant Examiner*—Brian Szmal
*Attorney, Agent, or Firm*—Thomas J. Connelly

[57] ABSTRACT

An expandable dome-shaped urinary incontinence device is disclosed along with a method of making the device. The device includes a resilient member and a non-absorbent which at least partially encloses the resilient member. The non-absorbent and the resilient member are formed into an elongated softwind having a first end, a second end, a first portion located adjacent to the first end, a second portion located adjacent to the second end and a third portion located between the first and second portions. The softwind is folded upon itself, such that the first and second ends are aligned adjacent to one another and a closed loop is formed. The first and second portions are then brought together to minimize the closed loop and the third portion is transformed into a dome shape. The softwind is then compressed into an elongated pledget having an insertion end and a trailing end with the resilient member located at least in the insertion end. The resilient member is capable of expanding at least a portion of the third portion to provide support for a woman's urethra when properly inserted into a woman's vagina. The method includes the steps of enclosing the resilient member by the non-absorbent, folding the two materials to form a softwind, folding the softwind such that a closed loop is formed and transforming the closed loop into a dome shape, and then compressing the softwind into an elongated pledget.

21 Claims, 5 Drawing Sheets

U.S. PATENT DOCUMENTS

| | | | |
|---|---|---|---|
| 5,336,208 | 8/1994 | Rosenbluth et al. | 604/329 |
| 5,483,976 | 1/1996 | McLaughlin et al. | 128/885 |
| 5,512,032 | 4/1996 | Kulisz et al. | 600/29 |
| 5,533,990 | 7/1996 | Yeo | 604/363 |
| 5,611,768 | 3/1997 | Tutrone, Jr. | 600/29 |
| 5,659,934 | 8/1997 | Jessup et al. | 28/120 |
| 5,752,525 | 5/1998 | Simon et al. | 128/885 |
| 5,755,906 | 5/1998 | Achter et al. | 156/217 |
| 5,785,640 | 7/1998 | Kresch et al. | 600/29 |
| 5,795,346 | 8/1998 | Achter et al. | 604/385.1 |
| 5,807,372 | 9/1998 | Balzar | 604/385.1 |
| 5,813,973 | 9/1998 | Gloth | 600/29 |
| 5,873,971 | 2/1999 | Balzar | 156/217 |

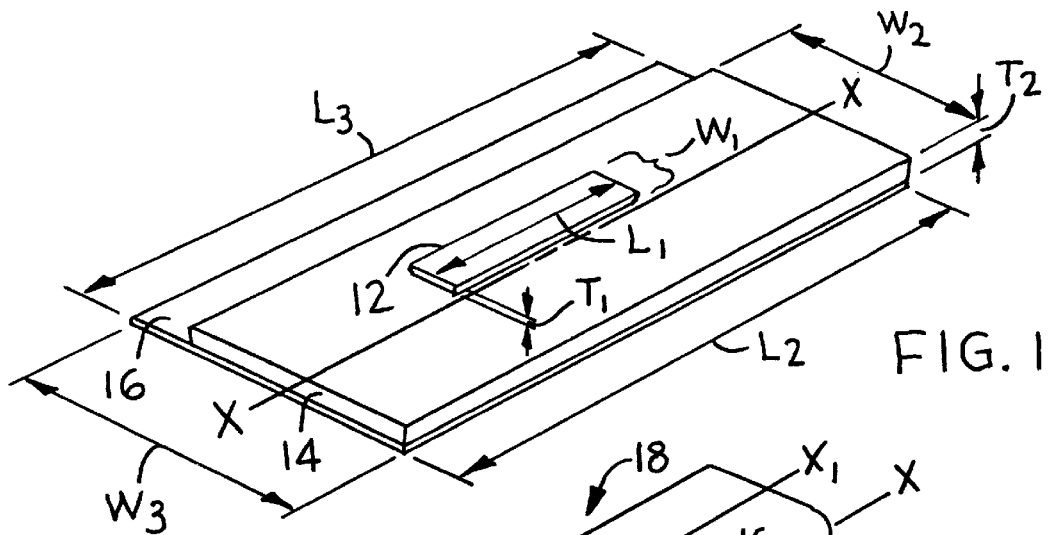
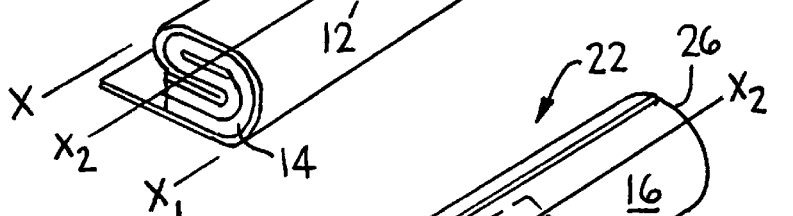
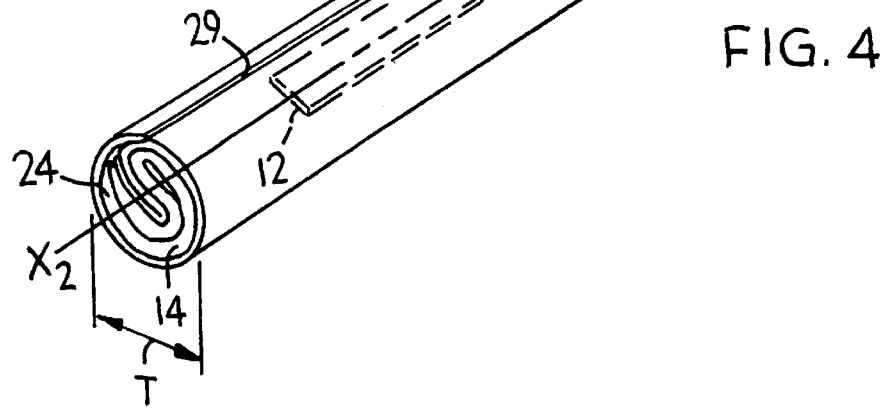

EXPANDABLE DOME-SHAPED URINARY INCONTINENCE DEVICE AND A METHOD OF MAKING THE SAME

FIELD OF THE INVENTION

This invention relates to an expandable dome-shaped urinary incontinence device and a method of making the device. More specifically, this invention relates to a non-absorbent urinary incontinence device which is designed to be placed in a woman's vagina for providing support to a woman's urethra to prevent the involuntary urine loss commonly associated with stress urinary incontinence.

BACKGROUND OF THE INVENTION

Some women, especially women who have given birth to one or more children, and older women, can experience incidences of involuntary urine loss due to stress urinary incontinence or combined stress and urge incontinence. A sneeze or cough can increase the intra-abdominal pressure impinging on a person's bladder and cause the involuntary release of urine. The frequency and severity of such urine loss can increase as the muscles and tissues near the urethrovaginal myofascial area grow weaker. It has also been recognized that the urinary sphincter muscle, which is located at the upper end of the urethra adjacent to the bladder, works well at sealing off the passing of urine from the bladder to the urethra when it has a round or circular cross-sectional configuration. However, when this passageway becomes distorted into a cross-sectional configuration having more of an elliptical or oval appearance, the sphincter muscle can not close properly, therefore, the tendency for involuntary urine loss increases.

As the world's female population ages, there is an ever increasing need for a non-surgical procedure to reduce the involuntary urine loss commonly associated with "stress urinary incontinence." Today, there are a number of products available for this purpose. Essentially all of these products can only be purchased with a prescription and they need to be physically inserted and/or adjusted by a medical doctor or a nurse practitioner in order to perform correctly. Currently, no products are commercially available, without a prescription, to prevent involuntary urine loss from stress urinary incontinence.

In view of the lack of commercially available, non-prescription urinary incontinence devices, it is recognized that there is a need for a urinary incontinence device which can be purchased without a prescription. There is also a need for a urinary incontinence device which is uncomplicated and therefor more user friendly and can be managed by the consumer without the intervention of a medical practitioner. Furthermore, there is a need for a urinary incontinence device which is easy for women to insert into and remove from their bodies, be more comfortable to wear and provide psychological and realistic assurance that it is capable of properly performing over an extended period of time.

SUMMARY OF THE INVENTION

Briefly, this invention relates to an expandable dome-shaped urinary incontinence device and a method of making the device. The device includes a resilient member and a non-absorbent which at least partially encloses the resilient member. The non-absorbent and the resilient member are formed into an elongated softwind having a first end, a second end, a first portion located adjacent to the first end, a second portion located adjacent to the second end and a third portion located between the first and second portions. The softwind is folded upon itself, such that the first and second ends are aligned adjacent to one another and a closed loop is formed. The first and second portions are then brought together to minimize the closed loop and the third portion is transformed into a dome shape. The softwind is then compressed into an elongated pledget having an insertion end and a trailing end with the resilient member located at least in the insertion end. The resilient member is capable of expanding at least a portion of the third portion to provide a supportive backdrop for a woman's urethra after being properly inserted into a woman's vagina.

The method of making the expandable dome-shaped urinary incontinence device includes the steps of cutting a non-absorbent into a configuration having a central longitudinal axis. Aligning a resilient member adjacent to the central longitudinal axis of the non-absorbent. Folding the non-absorbent around the resilient member, preferably at least two folds, to form an elongated softwind having a first end, a second end, a first portion located adjacent to the first end, a second portion located adjacent to the second end and a third portion located between the first and second portions. Then folding the softwind upon itself such that the first and second ends are aligned adjacent to one another and a closed loop is formed. The first and second portions are then brought together to minimize the closed loop and the third portion is transformed into a dome shape. The softwind is then compressed into an elongated pledget having an insertion end and a trailing end with the resilient member located at least in the insertion end. The resilient member is capable of expanding at least a portion of the third portion to provide support for a woman's urethra when the pledget has been properly inserted into a woman's vagina.

The general object of this invention is to provide an expandable dome-shaped urinary incontinence device and a method of making the device. A more specific object of this invention is to provide a non-absorbent urinary incontinence device which is designed to be placed in a woman's vagina for providing support to a woman's urethra to prevent involuntary urine loss commonly associated with stress urinary incontinence.

Another object of this invention is to provide an expandable dome-shaped urinary incontinence device which is simple to use, easy to insert and remove, and which is comfortable to wear.

A further object of this invention is to provide a method of making an expandable dome-shaped urinary incontinence device which is efficient and economical.

Still another object of this invention is to provide an expandable dome-shaped urinary incontinence device which can be purchased by a consumer without a prescription.

Still further, an object of this invention is to provide an expandable dome-shaped urinary incontinence device which can be used along with a sanitary napkin during a woman's menstrual period.

Other objects and advantages of the present invention will become more apparent to those skilled in the art in view of the following description and the accompanying drawings.

BRIEF DESCRIPTION OF THE DRAWINGS

FIG. 1 is a perspective view of a resilient member position on a non-absorbent and a cover.

FIG. 2 is a perspective view of the combination shown in FIG. 1 after being folded along it's longitudinal central axis.

FIG. 3 is a perspective view of the folded member shown in FIG. 2 after being folded a second time along it's longitudinal central axis.

FIG. 4 is a perspective view of the twice folded sofwind showing the cover overlapping itself.

DETAILED DESCRIPTION OF THE PREFERRED EMBODIMENTS

Figure 9:
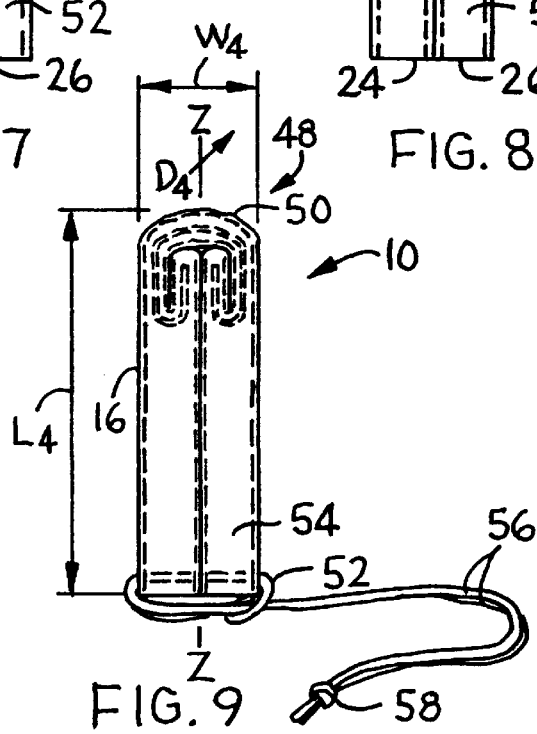
FIG. 9 is a side view of the softwind shown in FIG. 8 after it has been compressed into a pledget and has a withdrawal string attached to the first and second ends.

A urinary incontinence device 10, see FIG. 9, is depicted which is designed to be inserted into a woman's vagina and expand so as to relieve or eliminate the involuntary passage of urine through the urethra from the bladder. The expansion of the non-absorbent urinary incontinence device 10 provides a stable backdrop to the musculature and body tissue located near the urethro-vaginal myofascial area and causes the urethra to be compressed upon itself during episodes of increased intra-abdominal pressure. In addition, the expansion of the urinary incontinence device 10 in the vagina will assist the urinary sphincter muscle in maintaining a circular cross-sectional configuration. When this circular cross-sectional configuration is maintained, the sphincter muscle can close properly and decrease the tendency for the involuntary escape of urine due to stress urinary incontinence.

Referring to FIGS. 1–4, the expandable dome-shaped urinary incontinence device 10 includes a resilient member 12 and a non-absorbent 14. The resilient member 12 can be non-absorbent or at least partially absorbent of body fluids. However, there is no functional advantage to making the resilient member 12 absorbent because the urinary incontinence device 10 does not function in a similar manner as does a catamenial tampon. In fact, the urinary incontinence device 10 functions entirely different from an absorbent catamenial tampon.

The resilient member 12 can be a natural or synthetic material which has the ability to quickly recover or return to approximately its original shape and/or dimension. Such change in the resilient member 12 can be created by changes in the intra-abdominal pressure as a result of laughing, sneezing, coughing, or the like. A resilient material is a material which can return to or resume its original shape or position after being bent, stretched or compressed. The resilient member 12 should also exhibit elasticity and flexibility so that it can be stretched or compressed and still retain the capability of returning to approximately it's original shape.

Two natural materials from which the resilient member 12 can be formed include natural rubber and wool. The number of synthetic materials from which the resilient member 12 can be formed is much greater. Synthetic materials which can be used include polyolefins, polyurethanes, polyethylene oxide (PEO), polyvinyl alcohol (PVA) as well as blends thereof. The resilient member 12 can also be formed from resilient fibers constructed from polyolefin based fibers, polyethylene oxide fibers, hydrophobic rayon fibers and the like, which preferably will have characteristics similar to those of a resilient foam. The resilient fibers can be formed from twisted, curled or cross-linked cellulose fibers or a mixture thereof. Furthermore, the resilient member 12 may be formed from either an open cell or a closed cell foam.

The resilient member 12 can also be made from a wettable foam. An open cell foam which works well and has good resilient properties is commercially available under the trademark ACQUELL®. "ACQUELL" is sold by Sentinel Products Corporation having an office located at 70 Airport Road, Hyannis, Mass. 02601. A polyethylene closed cell foam having good flexibility characteristics also works well. This foam is commercially sold under the trademark VOLARA®. "VOLARA" is available from Voltex, a Division of Sekisui America Corporation having an office located at 100 Shepard Street, Lawrence, Mass. 01843.

The resilient member 12 should also be capable of having what is known as "dry and wet" expansion characteristics. In other words, the resilient member 12 should be made from a material which is capable of expanding or contracting back to or towards its original configuration in a dry state, a wet state or in a semi-dry-wet state. Dry expansion of the urinary incontinence device 10 is beneficial in that the device does not have to be wetted by body fluid before the resilient member 12 is capable of expanding within the vagina.

In FIG. 1, the resilient member 12 is depicted as a narrow strip of material which is rectangular in cross-section. However, the resilient member 12 can have a square, circular, oval or any other desired cross-sectional configuration. Preferably, the resilient member 12 will have a uniform thickness and width. If desired, the dimensions of the resilient member 12 do not have to be uniform. The narrow strip of resilient member 12 has a length $L_1$ which is less than the length $L_2$ of the non-absorbent 14. The length $L_1$ of the resilient member 12 can be less than about 75% of the length $L_2$ of the non-absorbent 14. Preferably the length $L_1$ of the resilient member 12 is less than about 50% of the length $L_2$ of the non-absorbent 14, and most preferably, the length $L_1$ of the resilient member 12 is less than about 40% of the length $L_2$ of the non-absorbent 14. However, the length $L_1$ of the resilient member 12 can be equal to the length $L_2$ of the non-absorbent 14, if desired. The resilient member 12 also has a width $W_1$ which can range between about 0.25 inches (about 6.4 millimeters) to about 1.5 inches (about 38.1 mm), preferably between about 0.5 inches (about 12.7 mm) and about 1 inch (about 25.4 mm), and more preferably, about 1 inch (about 25.4 mm). The resilient member 12 also has a thickness $T_1$ which can range between about 0.1 inches (about 2.5 mm) to about 1 inch (about 25.4 mm), preferably less than about 0.5 inches (about 12.7 mm), and most preferably, less than about 0.4 inches (about 10 mm).

When the resilient member 12 has a round or circular cross-sectional configuration, the diameter can range between about 0.25 inches (about 6.4 millimeters) to about 1.5 inches (about 38.1 mm), preferably, between about 0.25 inches (about 6.4 millimeters) to about 1 inch (about 25.4 mm), and most preferably, less than about 0.5 inches (about 12.7 mm). For odd cross-sectional shapes like an oval, a bilobal, a trilobal, an ellipse, etc. the larger dimension should be no greater than about 2 inches (about 50 mm).

Referring still to FIG. 1, the resilient member 12 is positioned upon a non-absorbent 14 such that it lies parallel and adjacent to the central longitudinal axis X—X of the non-absorbent 14. It does not matter as to which side of the central longitudinal axis X—X the resilient member 12 is aligned. For best results, the non-absorbent 14 should have a length $L_2$ which is equal to or greater in dimension than the length $L_1$ of the resilient member 12. In addition, the non-absorbent 14 should have a width $W_2$ which is about two to about eight times the width $W_1$ of the resilient member 12. Preferably, the width $W_2$ of the non-absorbent 14 is about four times the width $W_1$ of the resilient member 12. The thickness $T_2$ of the non-absorbent 14 can be less than, equal to or greater than the thickness $T_1$ of the resilient member 12. The non-absorbent 14 can be a single ply of material or can be constructed of two or more plies or layers.

The non-absorbent 14 is constructed from materials that exhibit little, and preferably, no absorbent characteristics. The non-absorbent 14 differs from a catamenial tampon in that it does not function to absorb body fluid. Instead, the non-absorbent 14 is designed to bridge across the vagina and support the musculature and body tissue located in the urethro-vaginal myofascial area. By doing so, the urethra can be compressed upon itself sufficiently to interrupt the flow of urine and support can be provided to the urinary sphincter muscle so that it can function properly.

For purposes of this invention, a non-absorbent is defined as a material wherein the fibers do not absorb significant quantities of moisture within the fiber itself. It is to be recognized that virtually all materials will absorb some small quantity of moisture. A fiber is considered to be non-absorbent for present purposes if it will intrinsically gain no more than about 6 percent in weight when a bone dry fiber is maintained at 21 C° and at 65 percent relative humidity for 24 hours. Non-absorbent materials include but are not limited to nylons, rayons, spun cellulose, LYCRA®, KEVLAR®, carbon fibers and the like. "LYCRA" and "KELVAR" are trademarks of E. I. DuPont de Nemours & Company which has an office at 1007 Market Street, Wilmington, Del. 19801. One such non-absorbent 14 is a web made from bicomponent fibers which are commercially available from Chisso Corporation having an office at 1411 Broadway, 35 th floor, New York, N.Y. Such fibers are sold under the name "Chisso ESC Bicomponent Fiber" and consist of a polypropylene core surrounded by a polyethylene sheath. Fibers that work well have a denier of 3 and are 38 millimeters in length. Other bicomponent fibers made from polypropylene, polyethylene, etc. are commercially available from suppliers such as Exxon and Dow Chemical, as well as from other vendors.

Alternatively, the non-absorbent 14 could be an absorbent material such as a cotton/rayon blend which has been chemically treated with a surfactant to make it non-absorbent. However, materials comprised of truly non-absorbent fibers work best.

Referring again to FIG. 1, the non-absorbent 14 is shown being positioned on a liquid permeable or liquid-impermeable cover 16. The cover 16 is an optional element and need not be present to form the urinary incontinence device 10. However, the cover 16 can provide a smooth outer surface which may or may not be chemically treated to facilitate insertion and/or removal into and out of a woman's vagina. When present, the cover 16 should have a length $L_3$ which is equal to or greater than the length $L_2$ of the non-absorbent 14. The cover 16 should have a width $W_3$ which is greater than the width $W_2$ of the non-absorbent 14. The purpose of the greater dimension for the width $W_3$ is that it allows the cover 16 to be folded over upon itself and be bonded to itself by heat, pressure, a combination of heat and pressure, or by some other conventional means known to those skilled in the art. If the cover 16 is formed from a material which does not readily bond to itself, an adhesive, glue or other bonding or fastening medium can be used. If desired, the cover 16 may be simply folded over upon itself.

The cover 16 can be either liquid-permeable or liquid-impermeable. When the cover 16 is liquid-impermeable, it serves to block body fluids from contacting the non-absorbent 14. Since the non-absorbent 14 is not designed to absorb any body fluid, it is not necessary that the cover be liquid-impermeable. Liquid permeable materials include woven and nonwoven materials having a porous substrate. Woven materials include textile fabrics which can be made from rayon, cotton, or polyolefins. The polyolefins can be either staple or continuous filaments. The nonwoven materials can include spunbond, bonded carded webs and hydroentangled webs. Spunbond and bonded carded webs are commercially sold by Kimberly-Clark Corporation having an office at 401 N. Lake street, Neenah, Wis. 54956. Another nonwoven material which can be used as the cover 16 is formed from 100 percent polyester fibers held together by a binder. This material is known as powder-bonded-carded web (PBCW). PBCW is commercially available from HDK Industries, Inc. having an office at 304 Arcadia Drive, Greenville, S.C. 29609.

The cover 16 can also be constructed from a liquid-impermeable material. A good liquid-impermeable material is a micro-embossed, polymeric film, such as polyethylene or polypropylene. Bicomponent films can also be used. A preferred liquid-impermeable material is polyethylene film. The thickness of the cover 16 can range from between about 0.1 mm to about 5 mm, preferably less than about 0.5 mm, and most preferably, less than about 0.2 mm.

Referring to FIGS. 1–4, the combination resilient member 12, non-absorbent 14 and cover 16, shown in FIG. 1, are folded along the central longitudinal axis X—X to obtain a folded member 18 having a central longitudinal axis $X_1$—$X_1$. The folded member 18, see FIG. 2, is then folded a second time along its central longitudinal axis $X_1$—$X_1$ to obtain an elongated softwind 20 having a central longitudinal axis $X_2$—$X_2$, see FIG. 3. The free end of the cover 16 can then be folded over upon itself and be bonded or attached, or left unattached if desired, to form an elongated softwind 22, see FIG. 4. The softwind 22 has a first end 24 and a second end 26.

It should be noted that the above discussion is directed to folding the layers of material 12, 14 and 16 upon themselves to form the softwind 22. However, the softwind 22 could be formed by rolling, wrapping, bending and/or manipulating one or more of the layers in a known fashion to obtain an elongated member having a cylindrical, rectangular or some other shape.

Figure 5:
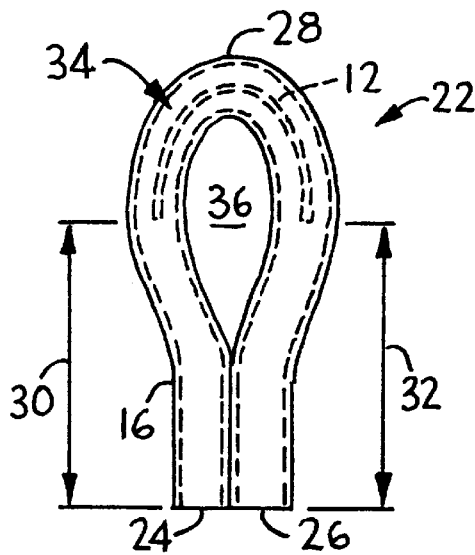
FIG. 5 is a side view of the softwind shown in FIG. 4 after it has been folded in half along its length and a closed loop is formed.

Referring to FIG. 5, the softwind 22 is folded or bent upon itself such that the first and second ends, 24 and 26 respectively, are aligned adjacent to one another and the softwind 22 contains a fold point 28. By being aligned "adjacent to one another" it is meant that the first and second ends, 24 and 26 respectively, are positioned side by side, parallel to one another, or offset axially or spaced radially apart from one another, or are positioned in some other type of arrangement whereby the first and second ends, 24 and 26 respectively, are close to one another. Preferably, the bonded or open edge 29 of the cover 16 should be positioned to the inside when the first and second ends, 24 and 26 respectively, are aligned adjacent to one another.

The softwind 22 will contain a first portion 30 located adjacent to the first end 24, a second portion 32 located adjacent to the second end 26 and a third portion 34 located between the first and second portions, 30 and 32 respectively. The first and second portions, 30 and 32 respectively, can have approximately the same length or differ in length, if desired. A length of from between about 1 inch (about 25 mm) to about 3 inches (about 76 mm) is adequate for each of the first and second portions, 30 and 32 respectively. A length of from between about 1.5 inches (about 33 mm) to about 2.5 inches (about 63 mm) is preferred for the first and second portions, 30 and 32 respectively. The third portion 34 can have a length less than, equal to or greater than the length of either the first or second portions, 30 and 32 respectively. Preferably, the third portion 34 will have a length which is slightly longer than either the first or second portions, 30 and 32 respectively. A typical softwind 22 from which the urinary incontinence device 10 is to be formed will have a length of from between about 5 inches (about 127 mm) to about 8 inches (about 203 mm), with a length of from between about 5 inches (about 127 mm) to about 6 inches (about 152 mm) being preferred. When the softwind 22 has a length of about 5 inches (about 127 mm), the first and second portions, 30 and 32 respectively, can have a length of about 1.5 inches (about 38 mm) and the third portion 34 can have a length of about 2 inches (about 51 mm).

In FIG. 5, one will notice that the resilient member 12 spans across the length of the third portion 34. However, the resilient member 12 can have a length which is shorter than, equal to, or longer than the length of the third portion 34. The purpose of the resilient member 12 is to expand and force the third portion 34 upward and/or outward so that it can bridge across the cross-sectional area of the user's vagina and contact the walls of the vagina. This action will retain the dome-shaped urinary incontinence device 10 in proper alignment within the vagina and create a force (pressure) which will help support the surrounding tissue located in the urethro-vaginal myofascial area and allow for sufficient pressure transmission across the urethra to interrupt the involuntary flow of urine when intra-abdominal pressure rises. Because of this, the resilient member 12 does not necessarily have to extend into the first and second portions, 30 and 32 respectively. The strength of the resilient member 12 will also dictate the size and shape needed to adequately open up the dome-shaped tip. Depending upon the material from which the resilient member 12 is constructed, it is advantageous to employ a resilient member 12 which has a length which extends across the entire length of the third portion 34. The resilient member 12 will assure that the softwind 22 will sufficiently open once it is placed within a woman's vagina.

Figure 6:
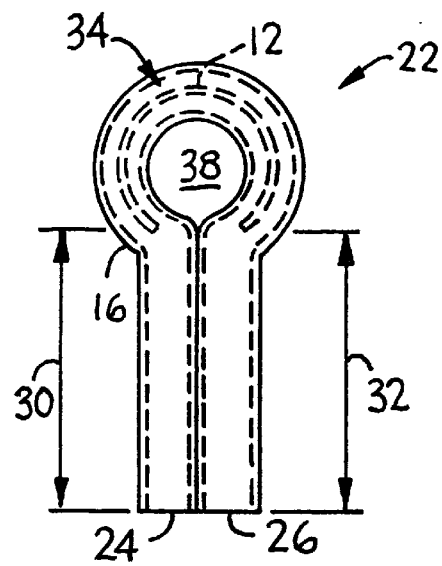
FIG. 6 is a side view of the folded softwind shown in FIG. 5 after the first and second portions are brought into contact with one another and a smaller closed loop is formed.
Figure 7:
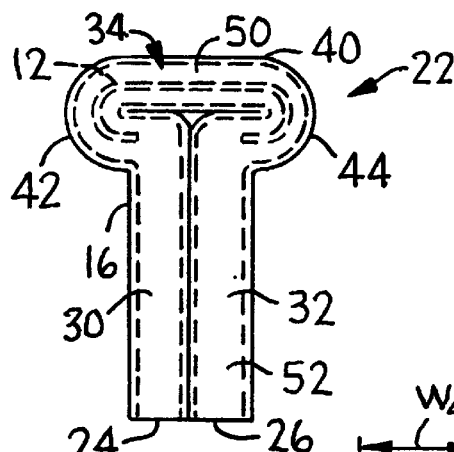
FIG. 7 is a side view of the softwind shown in FIG. 6 after the closed loop is transformed into a dome shape.

Referring to FIGS. 5, 6 and 7, when the softwind 22 is folded at point 28 and the first and second ends, 24 and 26 respectively, are aligned adjacent to one another, a closed loop 36 is formed. This closed loop 36 is made smaller or minimized to form a smaller closed loop 38 as the entire first and second portions, 30 and 32 respectively, are brought into contact with one another, see FIG. 6. The third portion 34 is then transformed into an arcuate shape 40 by pressing or squeezing the third portion 34 down against itself to form a semi-dome or mushroom-like profile, see FIG. 7. This arcuate shape 40 has opposite edges 42 and 44 which extend horizontally outward beyond the combined width of the first and second portions, 30 and 32 respectively.

Figure 8:
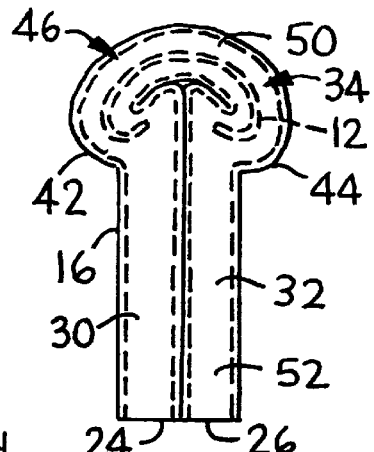
FIG. 8 is side view of the softwind shown in FIG. 7 after the edges of the dome shaped third portion are folded downward around the first and second portions.

Referring to FIG. 8, the edges 42 and 44 of the arcuate shape 40 are folded downward and/or inward to obtain a dome-shaped tip 46. By "dome-shaped" it is meant a hemispherical configuration resembling a dome structure. The dome shape tip 46 has a higher concentration of material and therefore is denser than the remaining first and second portions, 30 and 32 respectively. The dome-shaped tip 46 also forces the resilient member 12 to acquire an inverted U-shape or wishbone shape. Such a shape is conducive in facilitating the opening and expansion of the third portion 34.

Referring to FIG. 9, the softwind 22 is then compressed into a pledget 48 having an insertion end 50 and a trailing end 52. The pledget 48 can have any desired shape but preferably, it will have a generally cylindrical shape with a circular cross-sectional configuration. An alternative profile would be a rectangular cross-sectional configuration. The pledget 48 is an elongated member having a length $L_4$, a width $W_4$ and a depth $D_4$ which extends into the sheet. When the pledget 48 is round in cross-section, its diameter will be equal to the width dimension $W_4$ and depth $D_4$ dimension. The length $L_4$ of the pledget 48 can range from about 0.4 inches (about 10 mm) to about 4.7 inches (about 120 mm), preferably from between about 1.5 inches (about 38 mm) to about 2.5 inches (about 64 mm), and most preferably, the length $L_4$ is about 2 inches (about 51 mm). The width $W_4$ and depth $D_4$ can range from between about 0.2 inches (about 5 mm) to about 2.5 inches (about 64 mm), preferably from between about 0.5 inches (about 12.7 mm) to about 2.3 inches (about 60 mm). Most preferably, the width $W_4$ and depth $D_4$ of the pledget 48 is less than about 1.6 inches (about 40 mm).

Still referring to FIG. 9, the insertion end 50 of the pledget 48 is designed to be the first part of the pledget 48 which enters the woman's vaginal cavity. It should be noted that, while in use, the pledget 48 will be entirely positioned within the woman's vagina. Since the insertion end 50 contains the dome-shaped tip 46, the insertion end 50 will normally contain a greater amount of non-absorbent material than the trailing end 52. Even though a greater amount of non-absorbent 14 maybe present at the insertion end 50, the outside diameter of the insertion end 50 should be equal to the outside diameter of the trailing end 52. The amount of non-absorbent material in the insertion end 50 will have to be densified to a greater extent than the non-absorbent material making up the trailing end 52. By having a greater amount of non-absorbent 14 present at the insertion end 50, the urinary incontinence device 10 is better able to expand and support the musculature and the body tissue located adjacent to the urethra and facilitate urethral compression. This will eliminate the involuntary escape of urine through the urethra.

When the pledget 48 is formed, the resilient member 12, the non-absorbent 14 and the cover 16, if present, are all compressed. The pledget 48 can be compressed radially and lengthwise or it can be compressed only in the radial direction. The resilient member 12 should be located at least in the insertion end 50 of the pledget 48. The compression step should not detrimentally effect the function of the resilient member 12. In other words, the resilient member 12 has to be capable of expanding outward towards or to its original configuration once the urinary incontinence device 10 is inserted into a woman's vagina. The resilient member 12 must be capable of expanding at least a portion of the pledget 48 to provide support for a woman's urethra when properly inserted and positioned in a woman's vagina.

Still referring to FIG. 9, the compressed pledget 48 is pierced at its trailing end 52 to form an aperture or opening 54 which extends partially or completely through the first and second portions, 30 and 32 respectively. The aperture 54 can be formed perpendicular to the central longitudinal axis Z—Z or at an angle thereto. Preferably, the aperture 54 is spaced a short distance from the first and second ends, 24 and 26 respectively. The aperture 54 can be located a distance of from between about 0.1 inches (about 2.5 mm) to about 0.5 inches (about 12.7 mm) from the first and second ends, 24 and 26 respectively. Most preferably, the aperture 54 is located about 0.25 inches (about 6.4 mm) from each of the first and second ends, 24 and 26 respectively. The aperture 54 is designed to allow a withdrawal string 56 to be looped therethrough and be secured to the pledget 48. The withdrawal string 56 will assist in removing the expandable dome-shaped urinary incontinence device 10 from a woman's vagina. The withdrawal string 56 is attached to the non-absorbent 14, and preferably, to the first and second ends, 24 and 26 respectively, of the softwind 22. The aperture 54 can be formed with a needle, an awl or some other type of piercing device known to those skilled in the art. The withdrawal string 56 is threaded through the aperture 54 and looped upon itself so as to cinch it secure to the non-absorbent 14. The free ends of the withdrawal string 56 are then tied in a knot 58 to assure that the withdrawal string 56 will not separate from the pledget 48. The knot 58 also serves to prevent fraying of the withdrawal string 56 and to provide a place or point where a woman can grasp the withdrawal string 56 when she is ready to remove the expandable dome-shaped urinary incontinence device 10 from her vagina.

It should be noted that the withdrawal string 56 holds the first and second ends, 24 and 26 respectively, in direct contact with one another and will limit the amount they can expand while positioned within the woman's vagina. It should also be noted that the withdrawal string 56 can be secured to and/or attached to various areas of the pledget 48 and can pass through one or more of the resilient member 12, the non-absorbent 14, the cover 16, if present, or through all three members, if desired. The aperture 54 can alternatively be formed in the softwind 22 before it is compressed and the withdrawal string 56 can be attached either before the softwind 22 is compressed or after the softwind 22 is compressed into the pledget 48.

The withdrawal string 56 can be constructed from various types of threads or ribbons. A thread or ribbon made from 100 percent cotton fibers works well. The withdrawal string 56 should have a length which extends beyond the end of the expandable dome-shaped urinary incontinence device 10 of from between about 2 inches (about 51 mm) to about 8 inches (about 203 mm), preferably, from between about 4 inches (about 102 mm) to about 6 inches (about 152 mm), and most preferably, about 5 inches (about 127 mm). The withdrawal string 56 can be dyed and/or treated with an anti-wicking agent, such as wax, before being secured to the pledget 48. The anti-wicking agent will reduce and hopefully prevent body fluids from wicking along the withdrawal string 56 and contacting the inner surface of a woman's undergarment. A dry, clean withdrawal string 56 is preferred by the user, especially when she goes to remove the expandable dome-shaped urinary incontinence device 10 from her vagina.

Figure 10:
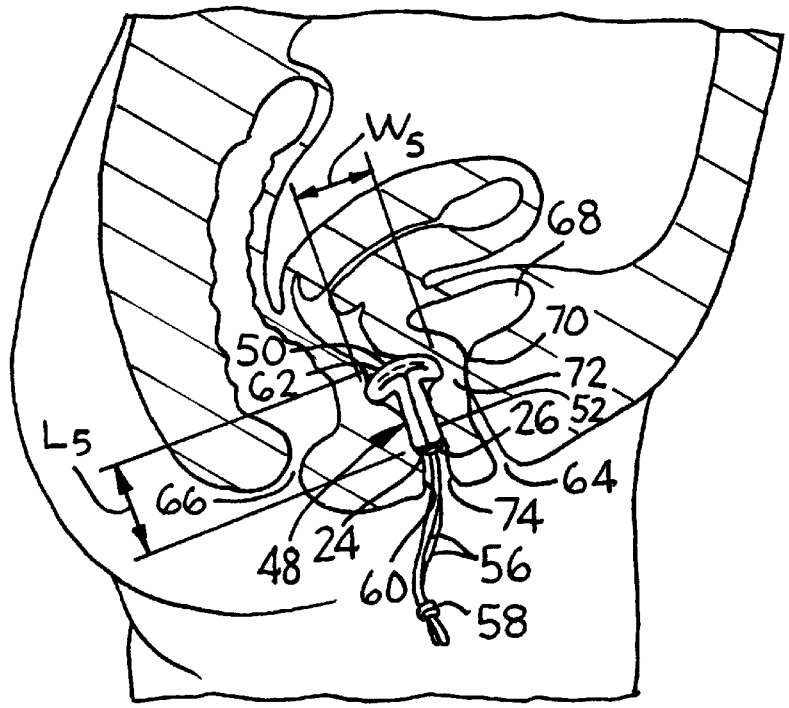
FIG. 10 is a mid-sagittal section of a human torso showing the expandable dome-shaped urinary incontinence device positioned in the vagina and expanded to provide support for the musculature and tissue near the urethro-vaginal myofascial region and the urethra.

Referring to FIG. 10, the compressed pledget 48 is depicted having been inserted into a woman's vagina 60 and the pledget 48 is shown in an expanded state 62. The expanded pledget 62 has a length $L_5$ and a diameter or width $W_5$. The expanded pledget 62 also has a mushroom-like tip at the insertion end 50 while the trailing end 52 has a cylindrical shape with the first and second ends, 24 and 26 respectively, positioned adjacent to one another. The first and second ends, 24 and 26 respectively, will stay together by the attachment of the withdrawal string 56. While within the vaginal cavity 60, the resilient member 12 will expand thereby causing the third portion 34 to spring or expand outward and/or upward and spread across a portion of the internal vaginal space. The urinary incontinence device 10 should be positioned below the cervix. The resilient, elastic and flexible characteristics of the resilient member 12 enables the pledget 48 to recover quickly from its compressed and deformed shape. This allows the urinary incontinence device 10 to intimately contact and conform more ideally to the space within the vaginal walls and press against the inside anterior and posterior and right and left lateral walls and convolutions of a woman's vagina 60.

A woman's urethra 64 is located adjacent to and anterior to the vagina 60. The woman's anus 66 is located on the posterior side of the vagina 60. The urethra 64 is a passageway which provides a means of removing urine from the woman's body. The urethra 64 is a conduit for removing urine which has accumulated in the woman's bladder 68 to an external orifice located at the lower end of the urethra 64. A urinary sphincter muscle 70 is situated at the upper portion of the urethra 64 adjacent to the bottom surface of the bladder 68. The sphincter muscle 70 operates to prevent the involuntary loss of urine. However, after birthing and with age the pelvic floor muscles begin to sag and the cross-sectional configuration of the sphincter muscle can change from a circular profile to a non-circular profile. Such a change increases the likelihood that a woman will experience involuntary urine loss. Between the vagina 60 and the urethra 64 is the urethro-vaginal myofascial area 72. This area 72 is made up of musculature and body tissue and the body tissue is extremely pliable. The vagina 60 contains a plurality of rugosities (not shown) which line its inside walls 74. The rugosities consist of wrinkles or creases in the body tissue which allows for expansion and contraction of the side walls 74 of the vagina 60.

Comparing the compressed pledget 48, shown in FIG. 9, to the expanded pledget 62, shown in FIG. 10, one will quickly recognize that the width $W_5$ of the expanded pledget 62 is much greater than the width $W_4$ of the compressed pledget 48. In addition, the shape of the expanded insertion end 50 is of a larger diameter or dimension than in the compressed pledget 48. However, the length $L_5$ of the expanded pledget 62 is approximately equal to the length $L_4$ of the compressed pledget 48. Preferably, the length $L_5$ of the expanded pledget 62 will be equal to or slightly larger than the length $L_4$ of the compressed pledget 48. The thickness (T) of the softwind 22 or dimension in the z-direction (see FIG. 4) should range from between about 0.5 inches (about 13 mm) to about 1.5 inches (about 38 mm). This distance will not change substantially once the urinary incontinence device 10 is inserted into the vagina 60. As the pledget 48 expands by the action of the resilient member 12, to the expanded state 62, the expanded pledget 62 will allow for pressure transmission across body tissue and in particular, in the urethro-vaginal myofascial area 72. This action will provide a stable backdrop to allow the woman's urethra 64 to become compressed upon itself when intra-abdominal pressure increases. In other words, a part of the urethra 64 which is about 1.5 inches (about 38 mm) long and through which urine flows, will be compressed or pinched upon itself thereby preventing the urine from passing through. In addition, support will be provided to the region near the sphincter muscle 70 so that it has a higher tendency to maintain a circular cross-sectional configuration and operate properly. One or both of these actions will reduce and/or prevent involuntary urine loss due to stress urinary incontinence.

Figure 11:
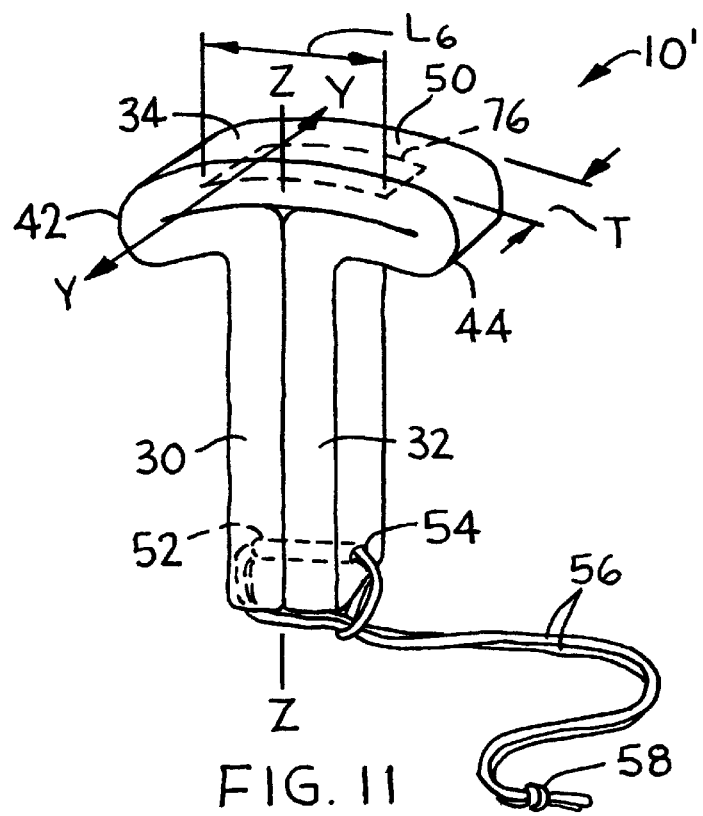
FIG. 11 is a perspective view of an alternative embodiment of an expandable dome-shaped urinary incontinence device having a resilient member which only extends along a portion of the dome-shaped insertion tip.

Referring to FIG. 11, an alternative embodiment of the expandable dome-shaped urinary incontinence device 10' is shown wherein no cover 16 is present and the insertion end 50 contains a resilient member 76 which has a shorter length than resilient member 12. The resilient member 76 is different from the resilient member 12 in that it is much shorter in length. The resilient member 76 can be constructed from the same materials as the resilient member 12 and can be shaped or configured in a similar manner. The length $L_6$ of the resilient member 76 can be about 50% of the length of the third portion 34, preferably less than about 40% of the length of the third portion 34, and most preferably, less than about 35% of the length of the third portion 34. In numerical terms, if the third portion 34 has a length of about 2 inches (about 51 mm), the length of the resilient member 76 can be about 1 inch (about 25 mm), preferably, less than about 0.8 inches (about 20 mm), and most preferably, less than about 0.7 inches (about 18 mm).

It should also be noted that the resilient member 76 can be offset to one side of the vertical axis Z—Z if desired. The important feature to remember is that the resilient members 12 or 76 should have sufficient resiliency to cause the dome-shaped tip 46 to expand outward and/or upward once the urinary incontinence device 10 or 10' has been inserted into a woman's vagina. The resilient and elastic properties of the resilient members 12 or 76 must be adequate to insure that the insertion end 50 will open and expand outward a sufficient amount so that the urinary incontinence device 10 or 10' can function properly.

Although not shown in any of the drawings, it is contemplated that the compressed pledget 48 can be housed in a paper, cardboard or plastic applicator to facilitate insertion of the urinary incontinence device 10 or 10' into a woman's vagina 60. The applicator can be identical to a tampon applicator, if desired, and can be constructed of one or more hollow tubes which will retain the urinary incontinence device 10 or 10' at a set diameter and/or cross-sectional configuration until the user is ready to use the product Furthermore, insertion of the urinary incontinence device 10 or 10' from the applicator into the human body can be accomplished by using a plunger, such as a two piece applicator, or by digital insertion whereby the user can use one of her fingers. One example of a tampon applicator is taught in U.S. Pat. No. 5,795,346 which issued to Achter et al. on Aug. 18, 1998 and is entitled: "TAMPON HAVING A RESILIENT MEMBER." This patent is incorporated by reference and made a part hereof.

METHOD

Figure 12:
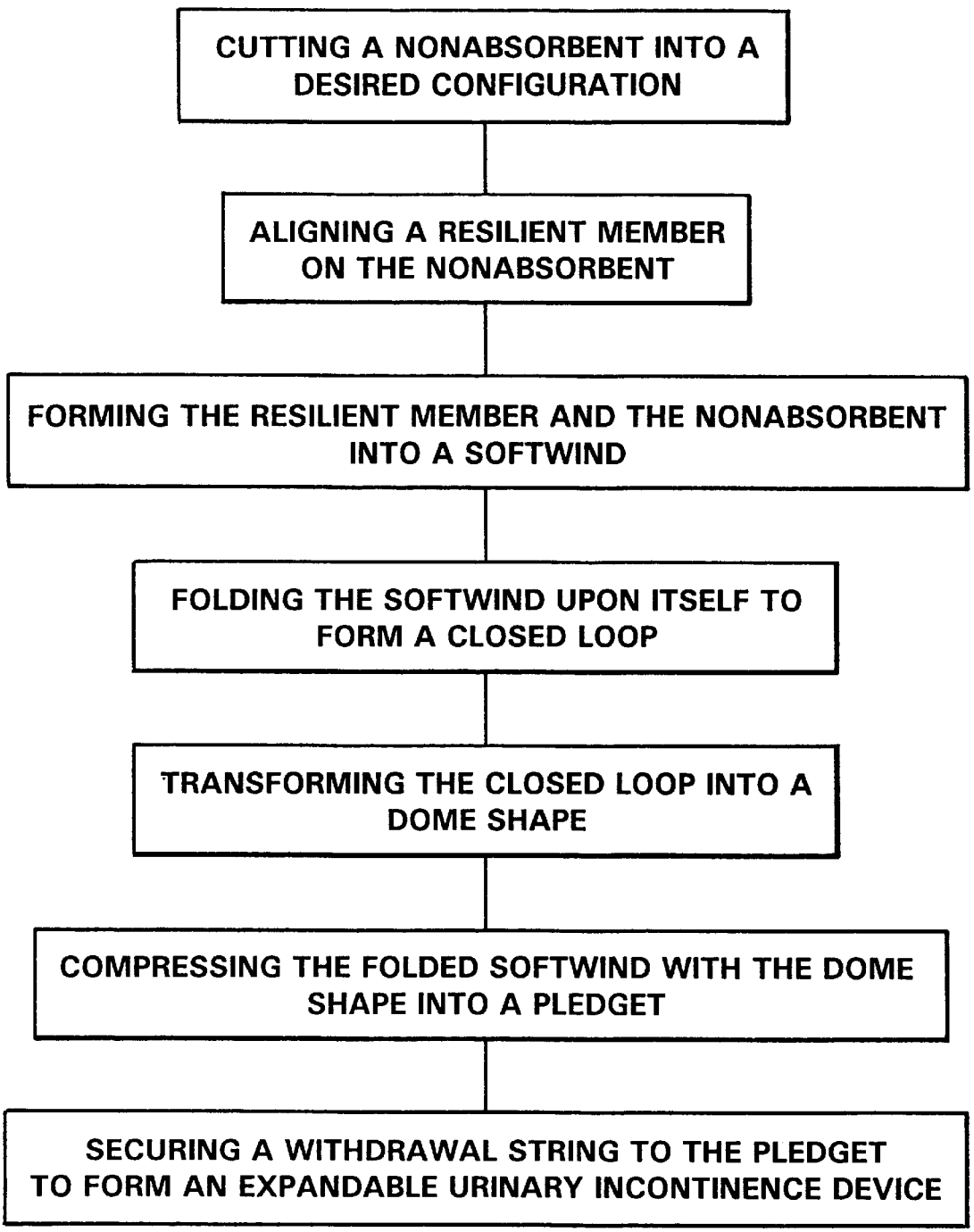
FIG. 12 is a flow diagram of a method of forming the expandable dome-shaped urinary incontinence device.
Figure 13:
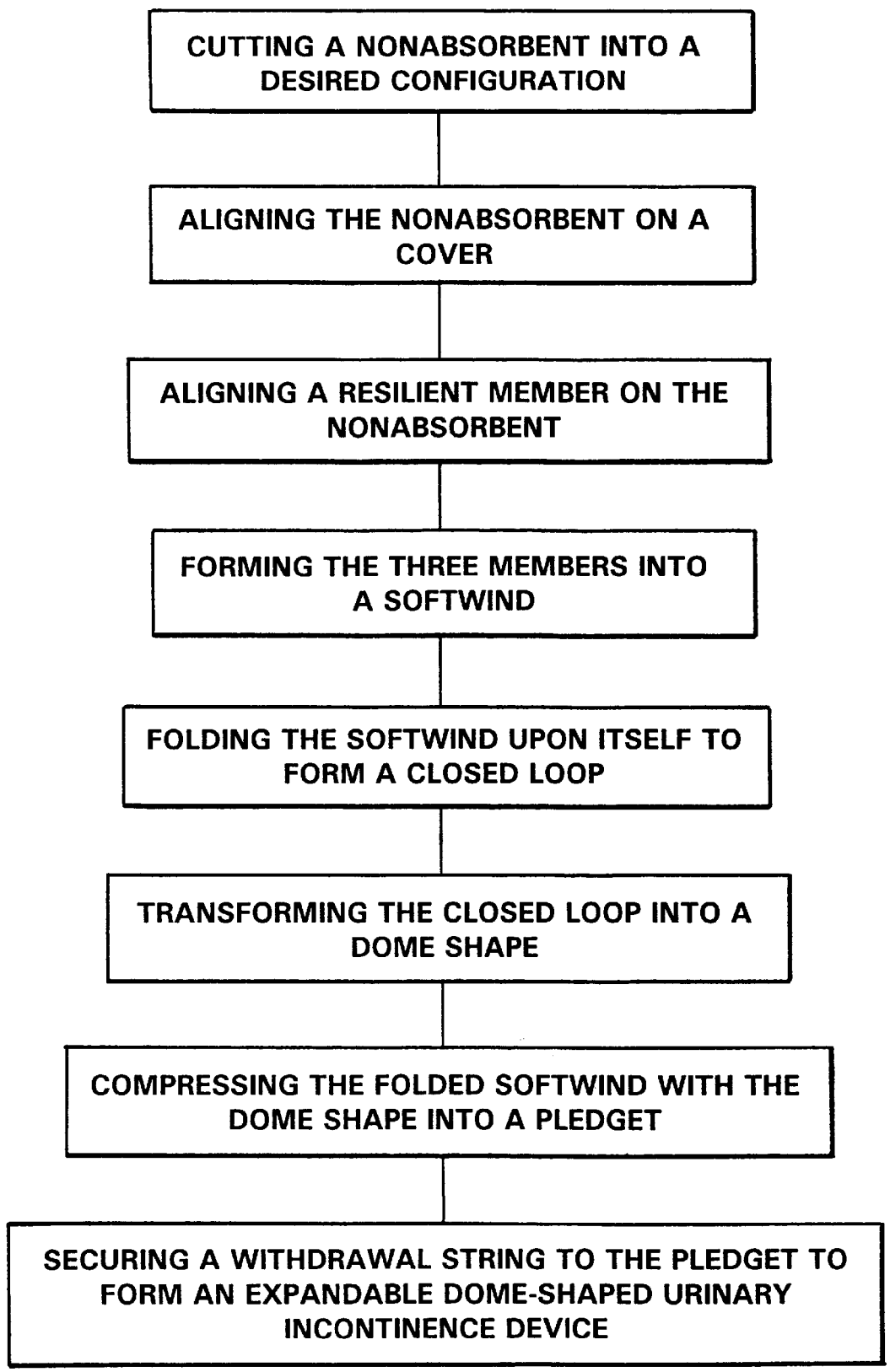
FIG. 13 is a flow diagram of an alternative method of forming an expandable dome-shaped urinary incontinence device.

The method of forming the expandable dome-shaped urinary incontinence device 10 or 10' will now be explained with reference to the flow diagrams shown in FIGS. 12 and 13. The method includes the steps of forming or cutting a non-absorbent 14 into a desired geometrical shape. A preferred shape for the non-absorbent 14 is a rectangle although many other shapes will work. The non-absorbent 14 will have a desired length, width and thickness. A resilient member 12 is positioned on or adjacent to one surface of the non-absorbent 14 to form an assembly of two elements. For best results, the resilient member 12 can be aligned adjacent to the central longitudinal axis X—X of the non-absorbent 14. By "adjacent to" it is meant that the resilient member 12 can have an edge which is coterminous with the central longitudinal axis X—X or the resilient member 12 can be offset or spaced apart from the central longitudinal axis X—X.

The non-absorbent 14 can be positioned on a cover material 16 such that the cover 16 is located adjacent to one surface of the non-absorbent 14 and the resilient member 12 is located adjacent to an opposite surface of the non-absorbent 14. The cover 16 is an optional feature and need not be present to make a useful urinary incontinence device 10 or 10'. The non-absorbent 14, along with the cover 16 are then folded around the resilient member 12. One method of folding is to fold the non-absorbent 14 and the cover 16, if present, transversely upon themselves such that a folded member 18 is formed and the resilient member 12 is now located adjacent to the longitudinal fold line $X_1$—$X_1$. The folded member 18 can then be folded a second time in a similar fashion to yield a softwind 20 as depicted in FIG. 3. When a cover 16 is present, the cover 16 can be wrapped or folded over upon itself and be bonded or attached to another portion of the cover 16 to form an elongated, cylindrical softwind 20, see FIG. 4.

It should be noted that the different materials forming the resilient member 12, the non-absorbent 14 and the cover 16 can be folded one or more times to obtain a predetermined diameter or cross-sectional configuration. Furthermore, the materials can be rolled, wrapped, bent or otherwise manipulated to arrange them into a softwind 20. Folding has been found to be a preferred way of accomplishing the formation of a softwind wherein the resilient member 12 is correctly aligned therein.

Once the softwind 22 is formed, it is folded or bent at a fold point 28 so that the first and second ends, 24 and 26 respectively, can be aligned adjacent to one another. Preferably, the softwind 22 is folded in half and a closed loop 36 is formed as the first and second portions, 30 and 32 are aligned parallel to one another, see FIG. 5. The first and second portions, 30 and 32 respectively, are then brought together along their entire length and the closed loop 36 is reduced in size to a smaller loop 38, see FIG. 6. At this point, the third portion 34 is pressed or squeezed downward upon itself in the direction of the first and second portions, 30 and 32 respectively. This action creates a semi-dome or mushroom-like profile 40, see FIG. 7, wherein the edges 42 and 44 of the third portion 34 extend outward beyond the thickness of the first and second portions, 30 and 32 respectively. The transformation of the third portion 34 into the semi-dome or mushroom-like profile 40 is continued by folding or bending the opposite edges 42 and 44 downward and/or inward against the outer surfaces of the first and second portions, 30 and 32 respectively, to form a dome-shaped tip 46, see FIG. 8. This dome-shaped tip 46 contains more non-absorbent material than is present in a similar area of the first and second portions, 30 and 32 respectively, and therefore is denser. The dome-shaped configuration 46 also contains the resilient member 12 or 76 which is needed to cause the insertion end 50 to expand outward and/or upward once the urinary incontinence device 10 or 10' is positioned within a woman's vagina.

After the dome-shaped tip 46 has been formed, the softwind 22 is compressed radially into a pledget 48, see FIG. 9. The softwind 22 can be compressed only in the radial direction or it can be compressed both axially and radially. Since the pledget 48 contains more material at the insertion end 50 than at the trailing end 52, the insertion end 50 will be denser since the pledget 48 has the same diameter or cross-sectional area throughout its entire length. This added material at the insertion end 50 will assure that as the pledget 48 opens and expands, once it is inserted into a woman's vagina, that it will provide a stable backdrop for the urethra and be able to provide the required pressure against the neighboring body tissues located in the urethro-vaginal myofascial area 72 so as to restrict the involuntary flow of urine through the urethra.

The compressed pledget 48 can then have a hole or aperture 54 formed through its trailing end 52 for receiving a withdrawal string 56. The aperture 54 can be formed with a needle, an awl or some other mechanical, electrical, chemical, hydraulic or pneumatic means. The aperture 54 should be aligned parallel to the first and second ends, 24 and 26 respectively, of the softwind 22 and be sufficiently spaced apart from the ends 24 and 26 to insure that as one pulls on the withdrawal string 56 that it will not tear through the material and be separated from the pledget 48. The withdrawal string 56 can be inserted through the aperture 54 and be looped upon itself to cinch it tight against the pledget 48. The pair of free ends of the withdrawal string 56 can then be tied in a knot 58 for added assurance that the withdrawal string 56 will not separate from the pledget 48.

It should be noted that the above discussion described piercing the pledget 48 to form the aperture 54. Another option would be to pierce the softwind 22. It should also be noted that FIG. 9 shows the aperture 54 passing through the non-absorbent 14 and the cover 16 while in FIG. 11 the aperture passes through only the non-absorbent 14 since no cover 16 is present.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A urinary incontinence device comprising:
   a) a resilient member; and
   b) a non-absorbent at least partially enclosing said resilient member, said non-absorbent and said resilient member being formed into an elongated softwind having a first end, a second end, a first portion located adjacent to said first end, a second portion located adjacent to said second end, and a third portion located between said first and second portions, said softwind being folded upon itself such that said first and second ends are aligned adjacent to one another and a closed loop is formed, said first and second portions being brought together to minimize said closed loop and said third portion is transformed into a dome shape, said softwind being compressed into an elongated pledget having an insertion end and a trailing end with said resilient member located at least in said insertion end and said resilient member capable of expanding at least a portion of said third portion to provide a supportive backdrop for a woman's urethra when inserted into a woman's vagina.

2. The urinary incontinence device of claim 1 wherein said third portion has a pair of opposite ends and said ends are bent downward toward said first and second ends of said first and second portions, respectively, to form said dome shape.

3. The urinary incontinence device of claim 1 wherein said third portion is longer in length than said first portion.

4. The urinary incontinence device of claim 1 wherein said third portion is longer in length than said second portion.

5. The urinary incontinence device of claim 1 wherein said resilient member is polyurethane.

6. The urinary incontinence device of claim 1 wherein said resilient member is natural rubber.

7. The urinary incontinence device of claim 1 wherein said resilient member is an open cell foam.

8. The urinary incontinence device of claim 1 wherein said resilient member is a closed cell foam.

9. The urinary incontinence device of claim 1 wherein said resilient member is formed from twisted, curled, or chemically cross-linked cellulose fibers or a mixture thereof.

10. A urinary incontinence device comprising:
    a) a resilient member;
    b) a non-absorbent at least partially enclosing said resilient member, said non-absorbent and said resilient member being formed into an elongated softwind having a first end, a second end, a first portion located adjacent to said first end, a second portion located adjacent to said second end and a third portion located between said first and second portions, said softwind being folded upon itself such that said first and second ends are aligned adjacent to one another and a closed loop is formed, said first and second portions being brought together to minimize said closed loop and said third portion is transformed into a dome shape, said softwind being compressed into an elongated pledget having an insertion end and a trailing end with said resilient member located at least in said insertion end and said resilient member capable of expanding at least a portion of said third portion to provide a supportive backdrop for a woman's urethra when inserted into a woman's vagina; and
    c) withdrawal means for removing said urinary incontinence device from the woman's vagina.

11. A urinary incontinence device comprising:
    a) a resilient member;
    b) a non-absorbent at least partially enclosing said resilient member, said non-absorbent and said resilient member being formed into an elongated softwind having a first end, a second end, a first portion located adjacent to said first end, a second portion located adjacent to said second end and a third portion located between said first and second portions, said softwind being folded upon itself such that said first and second ends are aligned adjacent to one another and a closed loop is formed, said first and second portions being brought together to minimize said closed loop and said third portion is transformed into a dome shape, said softwind being compressed into an elongated pledget having an insertion end and a trailing end with said resilient member located at least in said insertion end and said resilient member capable of expanding at least a portion of said third portion to provide a supportive backdrop for a woman's urethra when inserted into a woman's vagina;
    c) a cover enclosing said softwind; and
    d) withdrawal means for removing said urinary incontinence device from the woman's vagina.

12. The urinary incontinence device of claim 11 wherein said resilient member has a length which is about 50% of the length of said third portion.

13. The urinary incontinence device of claim 12 wherein said resilient member has a length which is less than about 40% of the length of said third portion.

14. The urinary incontinence device of claim 13 wherein said resilient member has a length which is less than about 35% of the length of said third portion.

15. The urinary incontinence device of claim 11 wherein said softwind is compressed only in a radial direction.

16. A method of making a urinary incontinence device, said method comprising the steps of:
   a) cutting a non-absorbent into a configuration having a central longitudinal axis;
   b) aligning a resilient member adjacent to said central longitudinal axis of said non-absorbent;
   c) forming said non-absorbent and said resilient member into an elongated softwind having a first end, a second end, a first portion located adjacent to said first end, a second portion located adjacent to said second end and a third portion located between said first and second portions;
   d) folding said softwind upon itself such that said first and second ends are aligned adjacent to one another and a closed loop is formed, said first and second portions being brought together to minimize said closed loop and said third portion is transformed into a dome shape; and
   e) compressing said softwind into an elongated pledget having an insertion end and a trailing end with said resilient member located at least in said insertion end, whereby said resilient member is capable of expanding at least a portion of said third portion to provide a supportive backdrop for a woman's urethra when said pledget is inserted into a woman's vagina.

17. The urinary incontinence device of claim 16 wherein said softwind is radially compressed.

18. The urinary incontinence device of claim 16 wherein said trailing end of said pledget is pierced to provide an opening for attaching withdrawal means.

19. The urinary incontinence device of claim 18 wherein a withdrawal string is inserted through said opening and looped upon itself and said withdrawal string has a pair of free ends which are tied together to prevent said withdrawal string from separating from said pledget.

20. The urinary incontinence device of claim 16 wherein said third portion has a pair of opposite edges and said edges are bent downward toward said first and second ends of said first and second portions, respectively, to form said dome shape.

21. A method of making a urinary incontinence device, said method comprising the steps of:
   a) cutting a non-absorbent into a rectangular configuration having a central longitudinal axis;
   b) aligning a rectangular strip of resilient member parallel and adjacent to said central longitudinal axis of said non-absorbent;
   c) folding said non-absorbent around said resilient member to form a folded member and folding said folded member again to form an elongated softwind having a first end and a second end;
   d) folding said softwind upon itself such that said first and second ends are aligned adjacent to one another and a closed loop is formed, said first and second portions being brought together to minimize said closed loop and said third portion is transformed into a dome shape;
   e) radially compressing said softwind into an elongated pledget having an insertion end and a trailing end with said resilient member located at least in said insertion end, whereby said resilient member is capable of expanding at least a portion of said pledget to provide a supportive backdrop for a woman's urethra when said pledget inserted into a woman's vagina; and
   f) securing a withdrawal string to said pledget to form a urinary incontinence device.

* * * * *